US00PP09996P

United States Patent [19]

Olesen et al.

[11] Patent Number: Plant 9,996

[45] Date of Patent: Aug. 12, 1997

[54] MINIATURE ROSE PLANT NAMED 'POULDEL'

[75] Inventors: Mogens N. Olesen; Pernille Olesen, both of Fredensborg, Denmark

[73] Assignee: Bear Creek Gardens, Inc., Medford, Oreg.

[21] Appl. No.: 606,895

[22] Filed: Feb. 21, 1996

[51] Int. Cl.[6] ..... A01H 5/00

[52] U.S. Cl. ..... Plt./8.2

[58] Field of Search ..... Plt./8.1, 8.2

*Primary Examiner*—Howard J. Locker

*Attorney, Agent, or Firm*—Klarquist Sparkman Campbell Leigh & Whinston, LLP

[57] ABSTRACT

A miniature rose plant, suitable as a pot rose, having non-fading light yellow flowers, rapid, even and compact growth, long shelf life and being readily propagated from softwood cuttings.

1 Drawing Sheet

The present invention relates to a new and distinct variety of rose plant of the miniature class which was originated by us by crossing the variety LENpi, unpatented, with an unnamed seedling.

The primary objective of this breeding was to produce a new rose variety having the compact vigorous growth of the pink miniature female parent combined with good flower form, light yellow flower color and dark green healthy foliage of the male unnamed seedling. The objective was substantially achieved, along with other desirable improvements, as evidenced by the following unique combination of characteristics that are outstanding in the new variety and that distinguish it from its parents, as well as from all other varieties of which we are aware:

1. Attractive, nonfading, light yellow flower color;
2. Rapid, even growth;
3. Compact size;
4. Ease of propagation from softwood cuttings; and
5. Long shelf life in bloom.

Asexual reproduction of this new variety by softwood cuttings, as performed at Wasco and Somis, Calif., and Fredensborg, Denmark, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—LENpi.

*Pollen parent.*—Unnamed seedling.

Classification:

*Botanical.*—Rosa hybrida.

*Commercial.*—Miniature.

FLOWER

Observations made from specimens grown in a greenhouse environment at Somis, Calif., and Fredensborg, Denmark.

Blooming habit: Continuous.

Bud:

*Size.*—¾ inch long when the petals start to unfurl.

*Form.*—The bud form is short.

*Color.*—When sepals first divide, bud color is Yellow Group 2D. When half blown, the upper sides of the petals are Yellow Group 4D; and the lower sides of the petals are Yellow Group 2D.

*Sepals.*—Color: Green Group 138A. Surface texture: Covered in fine hairs. There are three lightly appendaged sepals. There are two unappendaged sepals with hairy edges and glands.

*Receptacle.*—Color: Green Group 143C. Shape: Funnel. Size: Small (⅜"×¼"). Surface: Smooth.

*Peduncle.*—Length: Short (2–2¼"). Surface: Smooth with a few small glands. Color: Medium green. Strength: Stiff and erect.

Bloom:

*Size.*—Small. Average open size is 1¾–2".

*Borne.*—Singly, several together, and in pyramidal clusters of 3 flowers.

*Stem.*—Short and strong. Average length is about 6–8 inches.

*Form.*—When first open: High center. Permanence: Outer petals curl back.

*Petalage.*—Number of petals under normal conditions: 30.

*Color.*—The upper side of the petals is Yellow Group 4D. The reverse side of the petals is Yellow Group 2D. The base of each petal has a small Yellow Group 4B half moon at the point of attachment. The major color on the upper side is Yellow Group 4D.

*Variegations.*—Occasional greenish streak on the guard petals.

*Discoloration.*—The general tonality at the end of the first day: No change. At the end of the third day: No change. Flowers retain their color without fading until they drop at day 5 or 6.

*Fragrance.*—Moderate.

*Shelf life.*—Under low urban conditions, plant will remain in bloom for twelve or more days.

Petals:

*Texture.*—Thick and leathery.

*Shape.*—Round to oval.

*Form.*—Tips slightly recurved and edges slightly quilled.

*Arrangement.*—Imbricated, with many petaloids in the center.

*Persistence.*—Drops off cleanly.

*Lastingness.*—On the plant: Long (5 or 6 days). As a cut flower: Not tested.

Reproductive parts:

*Anthers.*—Size: Medium. Quantity: Few. Color: Yellow. Arrangement: Regular around styles and mixed with petaloids.

*Filaments.*—Color: Yellow.

*Pollen.*—Color: Lemon yellow.

*Styles.*—Color: Reddish.

*Stigmas.*—Color: Greenish white.

Form: Bush.

Growth: Vigorous, dwarf, upright, branching, and compact. Height of POULdel in full flower in a 5-inch pot is 9–11 inches.

Foliage: Number of leaflets of normal mid-stem leaves: 5.

*Size.*—Small (3½"×2").

*Quantity.*—Abundant.

*Color.*—New foliage: Very little anthocyanin. Upper: Green Group 143A. Lower: Green Group 143C. Old foliage: Upper: Green Group 139A. Lower: Green Group 139C.

Leaflets:

*Shape.*—Pointed oval.

*Texture.*—Upper side: Glossy and smooth.

*Edge.*—Serrated.

*Serration.*—Single and small.

*Petiole rachis.*—Color: Green.

*Petiole underside.*—Smooth with occasional prickles.

*Stipules.*—Short (¼").

*Disease resistance.*—Resistant to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Short (¼") and straight.

*Color when young.*—Red.

Small prickles:

*Quantity.*—On main stalks: None. On laterals: None.

We claim:

1. A new and distinct variety of rose plant of the miniature class, substantially as herein shown and described, characterized particularly as to novelty by the unique combination of its attractive, nonfading light yellow flowers; rapid, even growth; compact size; long shelf life; and ease of propagation from softwood cuttings.

* * * * *

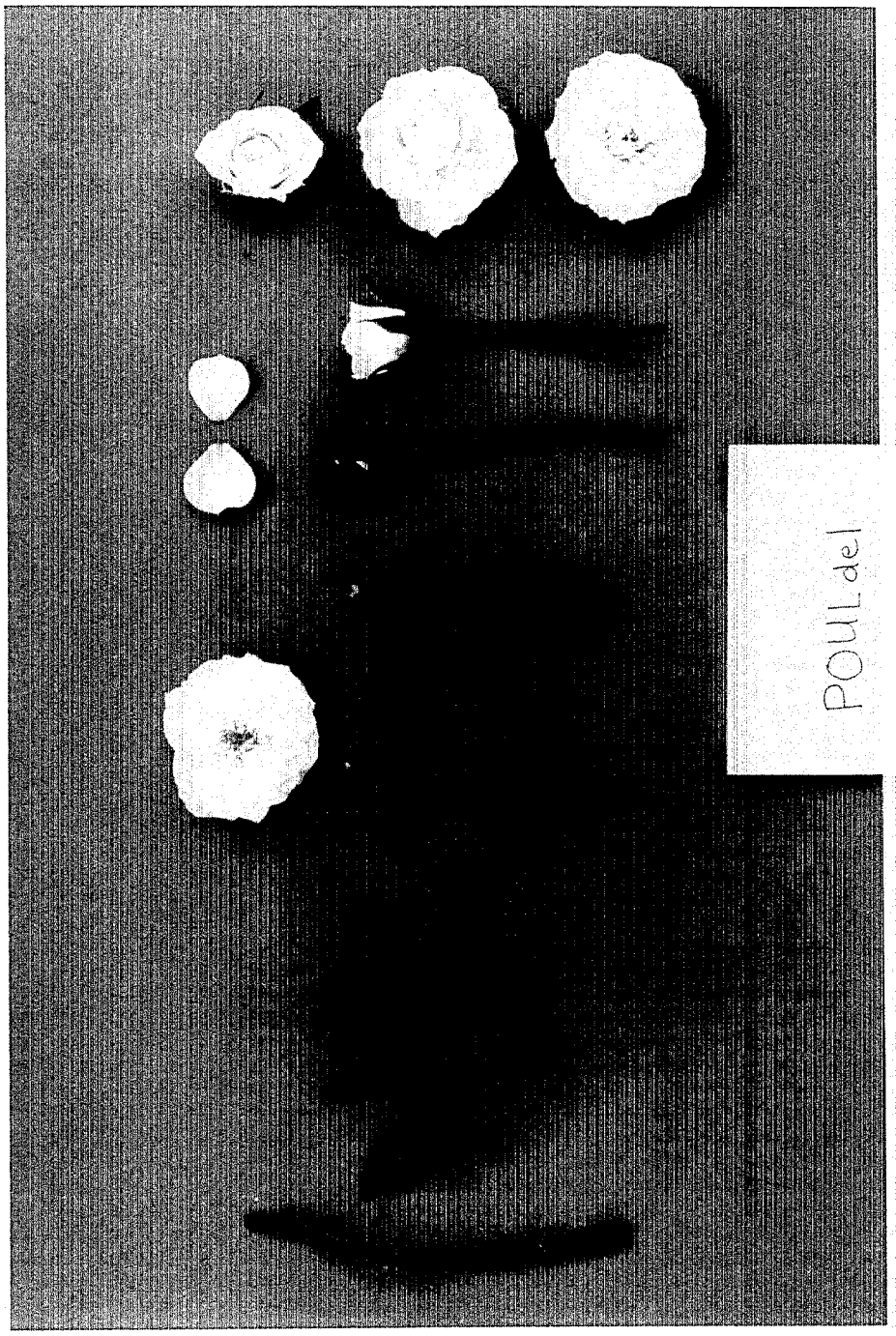
POULdel

UNITED STATES PATENT AND TRADEMARK OFFICE

CERTIFICATE OF CORRECTION

PATENT NO. : Plant 9,996

DATED : August 12, 1997

INVENTOR(S) : Mogens N. Olesen, et al.

It is certified that error appears in the above-identified patent and that said Letters Patent is hereby corrected as shown below:

Column 2, line 40, "low urban" should read --low light urban--.

Column 3, line 16, "of" should read --on--.

Signed and Sealed this

Thirtieth Day of December, 1997

Bruce Lehman

*Attest:*

BRUCE LEHMAN

*Attesting Officer*

*Commissioner of Patents and Trademarks*